(12) United States Patent
Petit

(10) Patent No.: US 11,439,779 B2
(45) Date of Patent: Sep. 13, 2022

(54) DEVICE FOR DISPENSING A FLUID PRODUCT

(71) Applicant: APTAR FRANCE SAS, Le Neubourg (FR)

(72) Inventor: Ludovic Petit, Vitot (FR)

(73) Assignee: APTAR FRANCE SAS, Le Neubourg (FR)

( * ) Notice: Subject to any disclaimer, the term of this patent is extended or adjusted under 35 U.S.C. 154(b) by 265 days.

(21) Appl. No.: 16/955,972

(22) PCT Filed: Dec. 18, 2018

(86) PCT No.: PCT/FR2018/053354
§ 371 (c)(1),
(2) Date: Jun. 19, 2020

(87) PCT Pub. No.: WO2019/122671
PCT Pub. Date: Jun. 27, 2019

(65) Prior Publication Data
US 2020/0316326 A1    Oct. 8, 2020

(30) Foreign Application Priority Data
Dec. 22, 2017 (FR) ................................. 1762963

(51) Int. Cl.
*A61M 15/08* (2006.01)
*A61M 11/00* (2006.01)
(Continued)

(52) U.S. Cl.
CPC .......... *A61M 15/08* (2013.01); *A61M 11/007* (2014.02); *B05B 11/0008* (2013.01); *B05B 11/02* (2013.01)

(58) Field of Classification Search
CPC . A61M 15/08; A61M 11/007; B05B 11/0008; B05B 11/02
(Continued)

(56) References Cited

U.S. PATENT DOCUMENTS 5,307,953 A * 5/1994 Regan ............... A61M 15/0036
                                                        604/203
5,944,222 A * 8/1999 Fuchs ................. B05B 11/0027
                                                        222/153.13
(Continued)

FOREIGN PATENT DOCUMENTS

| FR | 2775963 A1 | 9/1999 |
|---|---|---|
| WO | 00/71262 A1 | 11/2000 |
| WO | 2016/097603 A1 | 6/2016 |

OTHER PUBLICATIONS

International Preliminary Report on Patentability with translation of the Written Opinion dated Jul. 2, 2020 from the International Bureau in International Application No. PCT/FR2018/053354.
(Continued)

*Primary Examiner* — Jeremy Carroll
(74) *Attorney, Agent, or Firm* — Sughrue Mion, PLLC

(57) ABSTRACT

A fluid dispenser device having a reservoir (10) containing fluid; a dispenser head (20) provided with a dispenser orifice (21); and a piston (45; 70) for dispensing at least a portion of the fluid through the dispenser orifice (21). The reservoir (10) is closed in leaktight manner by a closure element (25) before actuation. The device includes a passage (40) for connecting the reservoir (10) to the dispenser orifice (21) during actuation, the passage (40) including a hollow sleeve (41) that is stationary relative to the dispenser head (20), for sliding around the closure element (25) during actuation, so as to open the passage (40).

15 Claims, 2 Drawing Sheets

(51) Int. Cl.
*B05B 11/00* (2006.01)
*B05B 11/02* (2006.01)

(58) Field of Classification Search
USPC .................................................. 128/200.14
See application file for complete search history.

(56) References Cited

U.S. PATENT DOCUMENTS

| | | | | |
|---|---|---|---|---|
| 6,321,942 | B1* | 11/2001 | Krampen | B05B 15/652 |
| | | | | 222/320 |
| 6,364,166 | B1* | 4/2002 | Ritsche | B05B 11/0027 |
| | | | | 222/384 |
| 6,708,846 | B1* | 3/2004 | Fuchs | A61M 11/007 |
| | | | | 222/386 |
| 2009/0294476 | A1* | 12/2009 | Koenig | B05B 11/0027 |
| | | | | 222/182 |
| 2020/0254465 | A1* | 8/2020 | Brouet | A61M 15/08 |

OTHER PUBLICATIONS

International Search Report (PCT/ISA/210) dated Mar. 14, 2019, issued by International Searching Authority in counterpart International Application No. PCT/FR2018/053354.

* cited by examiner

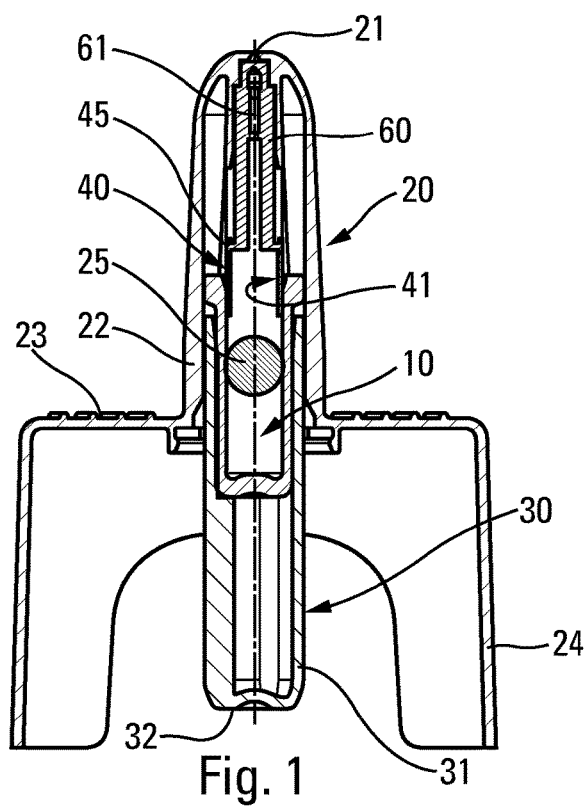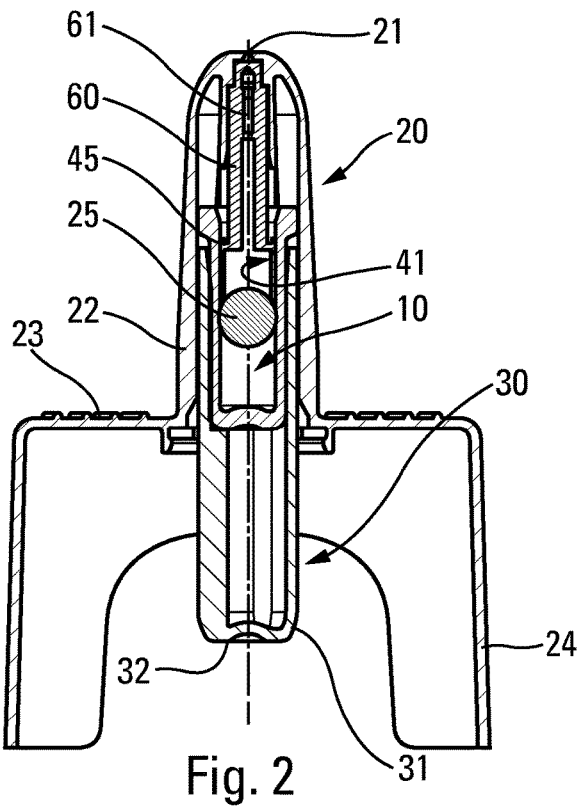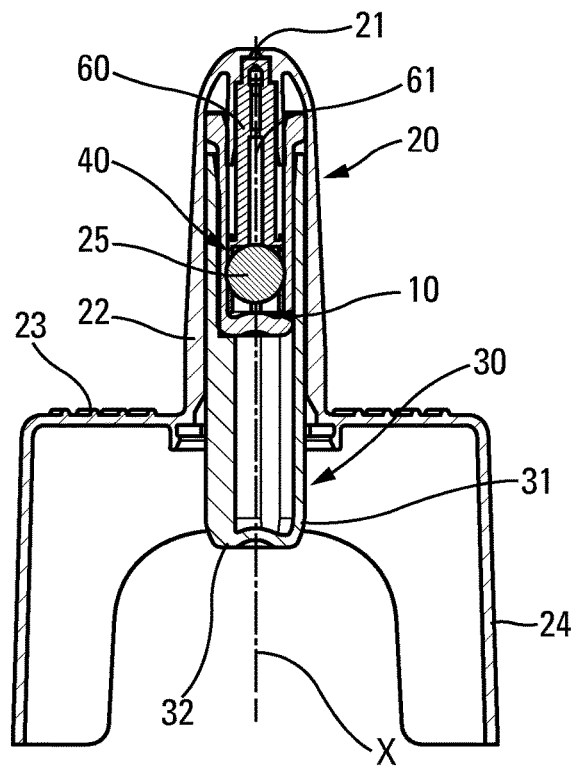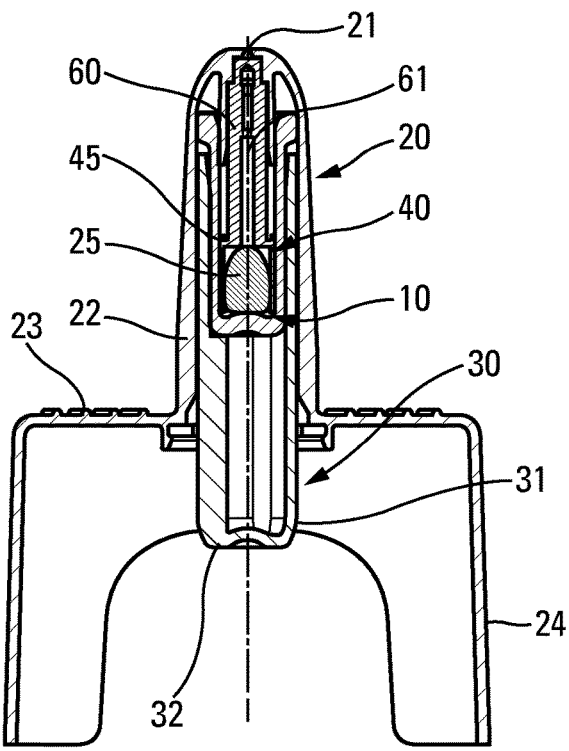

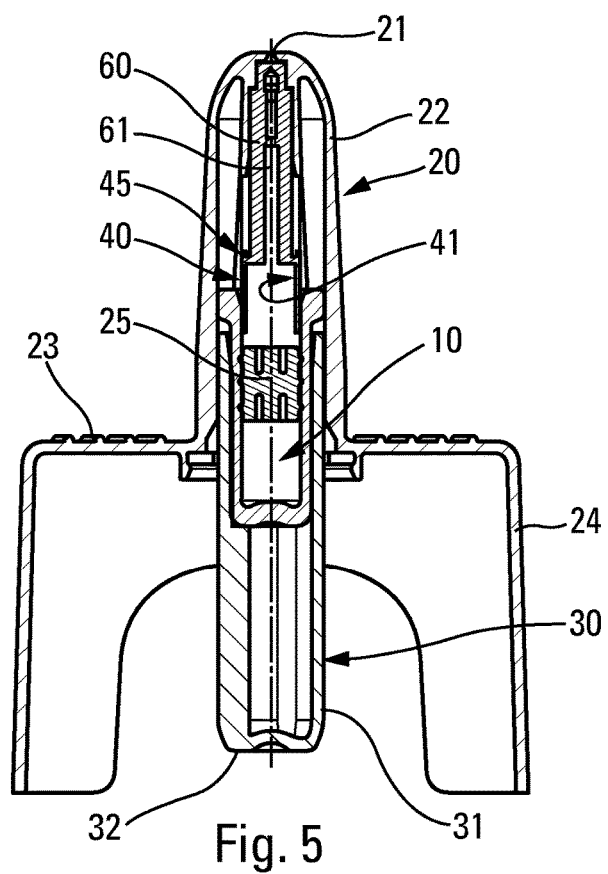
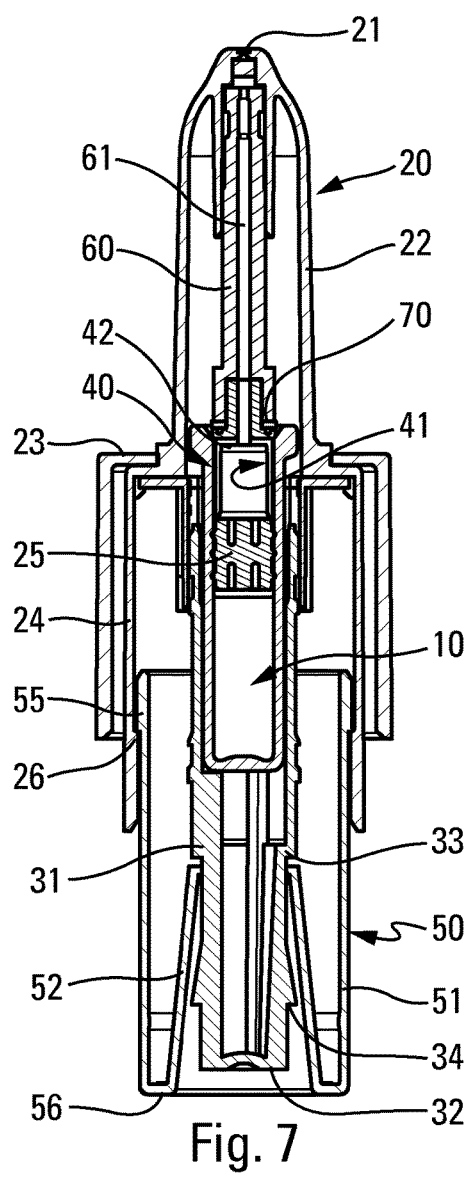
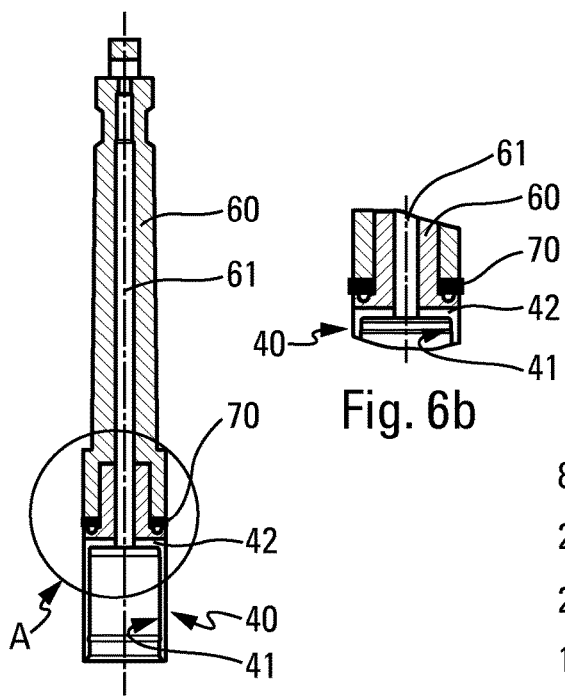
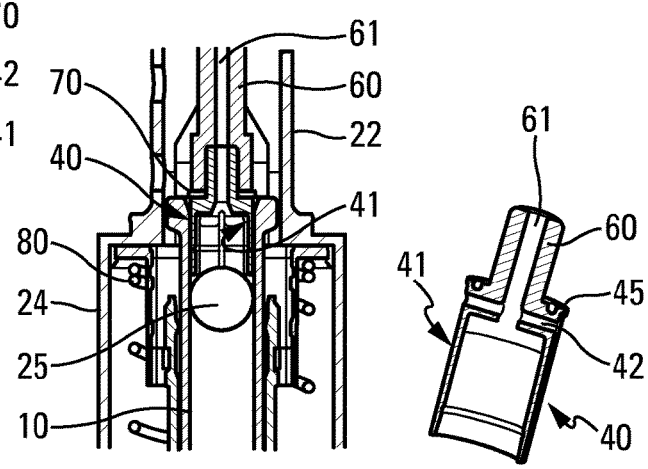
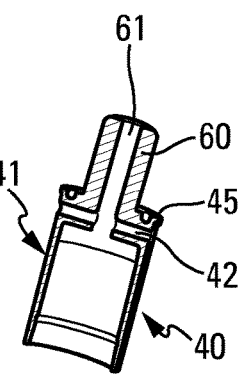
Fig. 5
Fig. 6a  Fig. 6b
Fig. 7
Fig. 8a  Fig. 8b

DEVICE FOR DISPENSING A FLUID PRODUCT

CROSS-REFERENCE TO RELATED APPLICATIONS

This is a National Stage of International Application of PCT/FR2018/053354 filed Dec. 18, 2018, claiming priority based on French Patent Application No. 1762963 filed on Dec. 22, 2017, the contents of all of which are incorporated herein by reference in their entirety.

The present invention relates to a fluid dispenser device.

More particularly, the present invention relates to a fluid dispenser device for dispensing a pharmaceutical fluid to a user, e.g. by means of a nasal spray. However, the present invention could also apply to dispenser devices for dispensing fragrance or cosmetics.

In this type of device, during actuation, a needle generally comes to perforate a stopper/piston. This technique presents in particular the risk of contaminating the fluid with particles of the stopper, released during perforating. In some circumstances, the particles may also cause the duct leading from the reservoir to the dispenser orifice to be blocked in full or in part, thus with a risk of the dispenser device malfunctioning. Putting the perforator needle into place, in particular in terms of its orientation and its retention in the device, may also turn out to be complex, consequently with the risk of the device malfunctioning.

Documents FR 2 775 963, WO 00/71262, and WO 2016/097603 describe prior-art devices.

An object of the present invention is to provide a fluid dispenser device that does not have the above-mentioned drawbacks.

More particularly, an object of the present invention is to provide a fluid dispenser device that avoids or limits any risk of contaminating the fluid.

Another object of the present invention is to provide such a device that avoids or limits any risk of the device malfunctioning.

Another object of the present invention is to provide such a device that is simple and inexpensive to manufacture and to assemble.

The present invention thus provides a fluid dispenser device comprising: a reservoir containing fluid; a dispenser head that is provided with a dispenser orifice; a piston for dispensing at least a portion of said fluid through said dispenser orifice; said reservoir being closed in leaktight manner by a closure element before actuation; said device including passage means for connecting said reservoir to said dispenser orifice during actuation, said passage means comprising a hollow sleeve that is stationary relative to said dispenser head, for sliding around said closure element during actuation, so as to open said passage means.

In a first advantageous variant, a radial gasket is assembled on said hollow sleeve so as to form a piston of the device, which piston co-operates in leaktight manner with said reservoir during actuation, so as to drive the fluid towards said dispenser orifice.

In a second advantageous variant, said hollow sleeve is formed integrally with a piston-forming lip that co-operates in leaktight manner with said reservoir during actuation, so as to drive the fluid towards said dispenser orifice.

Advantageously, said lip is formed at a proximal axial edge of said hollow sleeve.

Advantageously, said hollow sleeve and said lip are formed integrally with a hollow member that is arranged in said dispenser head, upstream from said dispenser orifice, said hollow member defining an expulsion channel.

In a variant said hollow sleeve is advantageously assembled in a hollow member that is arranged in said dispenser head, upstream from said dispenser orifice, said hollow member defining an expulsion channel.

Advantageously, said hollow member defines a spray profile directly upstream from said dispenser orifice.

Advantageously, said hollow sleeve includes an inner profile, such as one or more grooves or splines, so that when said hollow sleeve is arranged around said closure element, said inner profile creates one or more fluid passages around said closure element, so as to open said passage means.

In a variant, the outer cylindrical wall of said hollow sleeve advantageously has an outer profile, such as one or more grooves or splines, so that when said hollow sleeve is arranged around said closure element, said outer profile creates one or more fluid passages around said closure element, between the outside of said hollow sleeve and an inner wall of said reservoir, so as to open said passage means.

Advantageously, said hollow sleeve includes a radial channel for guiding the liquid towards said expulsion channel, with said piston arranged axially in proximal manner relative to said radial channel.

Advantageously, said closure element is a ball.

In a variant, said closure element is a cylindrical stopper.

Advantageously, said closure element is made out of elastomer or thermoplastic material.

In a first advantageous embodiment, said reservoir contains a single dose of fluid for dispensing during a single actuation of the device.

In a second advantageous embodiment, said reservoir contains two doses of fluid for dispensing during two successive actuations of the device.

These and other characteristics and advantages of the present invention appear more clearly from the following detailed description, given by way of non-limiting examples, and with reference to the accompanying drawings, and in which:

FIG. 1 is a diagrammatic section view of a fluid dispenser device in a first advantageous embodiment, shown in its rest position before actuation;

FIG. 2 is a view similar to the view in FIG. 1, showing the device at the start of actuation;

FIG. 3 is a view similar to the views in FIGS. 1 and 2, showing the device at the end of actuation;

FIG. 4 is a view similar to the view in FIG. 3, showing a first variant embodiment of the closure element;

FIG. 5 is a view similar to the view in FIG. 1, showing a second variant embodiment of the closure element;

FIG. 6a is a detail view in cross-section of a variant embodiment of the nozzle in FIGS. 1 to 5;

FIG. 6b is a larger-scale view of detail A in FIG. 6a;

FIG. 7 is a diagrammatic section view of a fluid dispenser device in a second advantageous embodiment of the present invention, shown in its rest position before actuation;

FIG. 8a is a cut-away detail view in perspective of an advantageous variant embodiment of the hollow sleeve; and FIG. 8b is a larger-scale detail view of another advantageous variant embodiment of the hollow sleeve.

The terms "proximal" and "distal" are relative to the dispenser orifice. The terms "axial" and "radial" are relative to the longitudinal central axis X shown in particular in FIG. 3. The terms "upstream" and "downstream" are relative to the direction of flow of the fluid during actuation.

FIGS. 1 to 5 show several variants of a first advantageous embodiment of the present invention.

In this first embodiment, a reservoir 10 containing fluid to be dispensed, typically a liquid, is arranged inside a body that forms a dispenser head 20. The dispenser head 20 includes a dispenser orifice 21 that is oriented axially in the embodiment in the figures, but that could be oriented in some other way, e.g. radially. The dispenser orifice 21 serves to dispense a dose of fluid out from said dispenser head 20 while the device is being actuated by a user.

Advantageously, the dispenser head 20 comprises: a nasal endpiece 22 that, at its proximal axial end, includes said dispenser orifice 21; and a side body 24 that is connected to said nasal endpiece 22 via a radial flange 23.

Advantageously, a hollow member 60 is arranged in the dispenser head 20, upstream from said dispenser orifice 21, said hollow member 60 defining an expulsion channel 61. Advantageously, said hollow member 60 may also define a spray profile directly upstream from said dispenser orifice 21.

In the embodiments in the figures, the reservoir 10 is formed by a body that is hollow and blind, including a single opening that is closed by a closure element 25 and containing a single dose of fluid to be dispensed in a single actuation of the device.

The closure element 25 may be a ball, as shown in FIGS. 1 to 3 and 8a. The ball could be made out of metal, but advantageously it is made out of elastomer or thermoplastic material, e.g. out of cyclic olefin copolymer (COC) or out of COC elastomer.

FIG. 4 shows a variant in which the closure element 25 has a shape that is modified in its distal portion, so as to limit the dead volume in the reservoir 10 at the end of actuation.

FIGS. 5 and 7 show another variant embodiment in which the closure element 25 forms a cylindrical stopper that is similar to a syringe piston.

It should be observed that the present invention can also be adapted to devices of the dual-dose type, containing two doses of fluid to be dispensed during two successive actuations of the device, as shown in FIG. 7.

Actuator means 30 are provided so as to make it possible to actuate the device.

In the variants in the figures, the actuator means 30 comprise an actuator body 31 that is movable relative to the dispenser head 20, said actuator body 31 co-operating with said reservoir 10 so as to move it axially relative to the dispenser head 20, towards the dispenser orifice 21.

The dispenser head 20 includes passage means 40 that, during actuation, connect the reservoir 10 to the dispenser orifice 21.

In the invention, the passage means 40 comprise a hollow sleeve 41 that is stationary relative to the dispenser head 20, and thus stationary relative to the dispenser orifice 21, and that is for co-operating with said closure element 25 during actuation, so as to open said passage means. As can be seen in the figures, during actuation, said hollow sleeve 41 comes to slide around said closure element 25.

Said hollow sleeve 41 may be formed integrally with a piston-forming lip 45 that co-operates in leaktight manner with the reservoir 10 during actuation, so as to drive the fluid towards the dispenser orifice 21. FIGS. 1 to 5 and 8b show such a variant. In this configuration, the lip 45 is formed at the proximal axial edge of said hollow sleeve 41. Advantageously, said hollow sleeve 41 and said lip 45 may be formed integrally with said hollow member 60, as shown in FIGS. 1 to 5.

In a variant, a radial gasket 70 may be assembled on said hollow sleeve 41, as can be seen in FIGS. 6a, 6b, 7, and 8a, in order to form the piston of the device.

In a variant, the hollow sleeve 41 and the piston, namely the lip 45 or the radial gasket 70, are assembled in said hollow member 60, as shown in FIGS. 6a to 8b.

In a first advantageous variant embodiment, shown in FIGS. 1 to 5 and 8a, said hollow sleeve 41 includes an inner profile, such as one or more grooves or splines, so that when said hollow sleeve 41 is arranged around said closure element 25, the inner profile creates one or more fluid passages around said closure element 25, so as to open the passage means 40.

In a second advantageous variant embodiment, shown in FIGS. 6a, 6b, 7, and 8b, the outer cylindrical wall of said hollow sleeve 41 has an outer profile, such as one or more grooves or splines, so that when said hollow sleeve 41 is arranged around said closure element 25, the outer profile creates one or more fluid passages around said closure element 25, between the outside of said hollow sleeve 41 and the inner wall of the reservoir 10, so as to open the passage means 40. In this configuration, a radial channel 42 is provided so as to guide the liquid towards the expulsion channel 61, with the piston 45, 70 arranged axially in proximal manner relative to said radial channel 42.

Operation of the device is described in detail below.

In conventional manner, in the examples shown in the figures, the user places two fingers on the radial flange 23 that is formed on the dispenser head 20, and presses with the thumb on the distal axial bottom wall 32 of said actuator body 31. During such actuation, the reservoir 10 is thus pushed axially towards the dispenser orifice 21, so that the hollow sleeve 41 slides around the closure element 25. The contents of the reservoir 10 are thus connected to the dispenser orifice 21, and the user pressing on the actuator body 31 moves the piston 45, 70 in the reservoir 10 so as to dispense the fluid.

In another embodiment that is not shown in the drawings, the reservoir need not be formed by a hollow and blind body that includes only one opening, but may be formed by a hollow cylinder that is open axially at both ends. The cylinder would thus be closed at the proximal end by a first closure element and at the distal end by a second closure element, the volume defined between said two closure elements containing the fluid to be dispensed. When the user actuates the device, the user presses axially on the actuator body so as to slide it axially towards the dispenser orifice, as described above. This causes the second closure element to move inside the reservoir. However, since the fluid is incompressible, the movement of the second closure element thus moves the first closure element towards the hollow sleeve, which is stationary. The first closure element is thus surrounded by said hollow sleeve and the contents of the reservoir are dispensed through the passage formed either between said hollow sleeve and said first closure element, or between said hollow sleeve and said reservoir, with the second closure element thus acting as a piston.

As described above, the invention can also apply to a device of the dual-dose type, as shown in FIG. 7, forming a second embodiment. In this configuration, the contents of the reservoir would be dispensed in two successive actuations. Document WO 2014/147329 describes an example of a dual-dose device.

In the embodiment in FIG. 7, an outer body 50 is assembled around the actuator body 31, said outer body 50 comprising a cylindrical sleeve 51 and at least one sloping tab 52 that is adapted to co-operate with projections 33, 34 of the actuator body 31 in order to perform successive actuations. The user thus presses preferably on the bottom axial edge 56 of said outer body so as to actuate the device. Advantageously, said outer body 50 is retained axially on said dispenser head 20 by co-operation between the proximal axial end 55 of said cylindrical sleeve 51 and a shoulder 26 provided in said side body 24 of said dispenser head 20. A return spring 80, shown in FIG. 8a, is mounted between the outer body 50 and the dispenser head 20, so as to return said outer body 50 into its start position after each actuation.

Naturally, other variant embodiments may also be envisaged, without going beyond the ambit of the present invention, as defined by the accompanying claims.

The invention claimed is:

1. A fluid dispenser device comprising: a reservoir (10) containing fluid; a dispenser head (20) that is provided with a dispenser orifice (21); a piston (45; 70) for dispensing at least a portion of said fluid through said dispenser orifice (21); said reservoir (10) being closed in leaktight manner by a closure element (25) before actuation; said device including passage means (40) for connecting said reservoir (10) to said dispenser orifice (21) during actuation, the device being characterized in that said passage means (40) comprise a hollow sleeve (41) that is stationary relative to said dispenser head (20), for sliding around said closure element (25) during actuation, so as to open said passage means (40).

2. A device according to claim 1, wherein a radial gasket (70) is assembled on said hollow sleeve (41) so as to form a piston of the device, which piston co-operates in leaktight manner with said reservoir (10) during actuation, so as to drive the fluid towards said dispenser orifice (21).

3. A device according to claim 1, wherein said hollow sleeve (41) is formed integrally with a piston-forming lip (45) that co-operates in leaktight manner with said reservoir (10) during actuation, so as to drive the fluid towards said dispenser orifice (21).

4. A device according to claim 3, wherein said lip (45) is formed at a proximal axial edge of said hollow sleeve (41).

5. A device according to claim 3, wherein said hollow sleeve (41) and said lip (45) are formed integrally with a hollow member (60) that is arranged in said dispenser head (20), upstream from said dispenser orifice (21), said hollow member (60) defining an expulsion channel (61).

6. A device according to claim 5, wherein said hollow member (60) defines a spray profile directly upstream from said dispenser orifice (21).

7. A device according to claim 1, wherein said hollow sleeve (41) is assembled in a hollow member (60) that is arranged in said dispenser head (20), upstream from said dispenser orifice (21), said hollow member (60) defining an expulsion channel (61).

8. A device according to claim 1, wherein said hollow sleeve (41) includes an inner profile, such as one or more grooves or splines, so that when said hollow sleeve (41) is arranged around said closure element (25), said inner profile creates one or more fluid passages around said closure element (25), so as to open said passage means (40).

9. A device according to claim 1, wherein the outer cylindrical wall of said hollow sleeve (41) has an outer profile, such as one or more grooves or splines, so that when said hollow sleeve (41) is arranged around said closure element (25), said outer profile creates one or more fluid passages around said closure element (25), between the outside of said hollow sleeve (41) and an inner wall of said reservoir (10), so as to open said passage means (40).

10. A device according to claim 9, wherein said hollow sleeve (41) is formed integrally with a piston-forming lip (45) that co-operates in leaktight manner with said reservoir (10) during actuation, so as to drive the fluid towards said dispenser orifice (21);

wherein said hollow sleeve (41) and said lip (45) are formed integrally with a hollow member (60) that is arranged in said dispenser head (20), upstream from said dispenser orifice (21), said hollow member (60) defining an expulsion channel (61); and wherein said hollow sleeve (41) includes a radial channel (42) for guiding the liquid towards said expulsion channel (61), with said piston (45, 70) arranged axially in proximal manner relative to said radial channel (42).

11. A device according to claim 1, wherein said closure element (25) is a ball.

12. A device according to claim 1, wherein said closure element (25) is a cylindrical stopper.

13. A device according to claim 1, wherein said closure element (25) is made out of elastomer or thermoplastic material.

14. A device according to claim 1, wherein said reservoir (10) contains a single dose of fluid for dispensing during a single actuation of the device.

15. A device according to claim 1, wherein said reservoir (10) contains two doses of fluid for dispensing during two successive actuations of the device.

* * * * *